United States Patent [19]

Logan et al.

[11] 4,091,285

[45] May 23, 1978

[54] TRAVERSE AND ROTATE CT SCANNER HAVING ROTATIONAL STEP THROUGH A MULTIPLE OF THE FAN ANGLE

[75] Inventors: Allan Beattie Logan, London; Robin Geoffrey Marsh, Reading; Ian Alexander Fleming, Maidenhead, all of England

[73] Assignee: EMI Limited, Hayes, England

[21] Appl. No.: 742,709

[22] Filed: Nov. 17, 1976

[30] Foreign Application Priority Data

Dec. 2, 1975 United Kingdom ............... 49349/75

[51] Int. Cl.² .......................... A61B 6/02; H05G 1/30
[52] U.S. Cl. ................................ 250/360; 250/445 T
[58] Field of Search ............................ 250/445 T, 360

[56] References Cited

U.S. PATENT DOCUMENTS 3,973,128 8/1976 Lemay ............................. 250/445 T
4,010,371 3/1977 Lemay ............................. 250/445 T Primary Examiner—Davis L. Willis
Assistant Examiner—T. N. Grigsby
Attorney, Agent, or Firm—Cooper, Dunham, Clark, Griffin & Moran

[57] ABSTRACT

In a medical radiographic apparatus, of the type in which a fan of radiation and detectors receiving the radiation along pencil beams in the fan are traversed laterally in relation to a slice of the patient's body and orbited about an axis intersecting the slice, an angular step between each lateral scan is usually substantially equal to the angle subtended by the radiation at its source. It is proposed to arrange the angular step to be a multiple of the angle subtended by the fan, thus leaving gaps in the range of angular position taken by beams of the fan. The gaps are filled in the course of an extended orbital motion.

5 Claims, 2 Drawing Figures

TRAVERSE AND ROTATE CT SCANNER HAVING ROTATIONAL STEP THROUGH A MULTIPLE OF THE FAN ANGLE

This invention relates to a method of and apparatus for constructing a representation of the variation of absorption of a planar slice of a body with respect to penetrating radiation such as X- or γ- radiation.

In U.S. Pat. No. 3,778,614 methods of and apparatus for constructing such a representation are described. According to one example described in that specification, a suitable source of radiation provides a pencil beam of radiation and a suitable detector is arranged to provide a measure of the absorption suffered by the beam in passing through the body. The source and detector are each provided with a scanning movement, relative to the body, to provide such a measure of absorption for each of a plurality of substantially parallel pencil beams of radiation at each of a plurality of inclinations in the plane of the slice. Those measurements of absorption are then processed by suitable means to provide a distribution of absorption coefficients for the said slice. To provide the required plurality of beams the source and detector are reciprocated in the plane of the slice and orbited in steps about a common axis normal to that plane.

The processing may be performed, for example, in the manner described in the aforementioned specification or in the manner described in U.S. Pat. No. 3,924,129.

In U.S. Pat. No. 3,946,234 there is described a variation of the apparatus of the said U.S. Pat. No. 3,778,614, for the same purpose, in which a source of radiation is arranged to provide a beam of radiation which has a wide angular spread in the plane of the slice. That beam is divided into a plurality of pencil beams by suitable collimators and an array of detectors is provided to measure the intensity of each of those beams after passage through the body. Scanning motions as described hereinbefore are further imposed on the source and detectors. As a result of the reciprocating motion the array of detectors provides absorption information relating to a plurality of sets of parallel beams of radiation, the sets being angularly spaced by the angular separation of the beams of the fan. To provide further sets of beams at different angles the orbital step between each reciprocating movement is then through a relatively larger step substantially equal to the total angular spread of the fan of radiation. In practice the orbital step is greater than that angular spread by an angle equal to the said angular separation since otherwise certain parallel sets of beam paths would be provided twice, by beams at opposite ends to the fan. To provide an even angular distribution of such parallel sets of beams over all angles relative to the body the orbital motion continues through 180°, less the said angular spread, since a beam path cannot be significantly distinguished by the direction of travel of the radiation.

According to the invention there is provided an apparatus for examining a slice of a body by means of penetrating radiation including a source of a substantially planar fan shaped spread of radiation arranged to irradiate the slice, a plurality of detectors co-operating with respective collimators to determine the intensity of the radiation transmitted along a plurality of beams within said fan shaped spread, means for scanning the source and detectors to scan the said fan shaped spread laterally in the said slice to provide determinations of the intensity of radiation transmitted along a plurality of sets of substantially parallel paths, each set provided by one of said detectors in the course of the lateral scan and means for orbiting said source and detectors between successive lateral scans about a common axis intersecting the said slice wherein the angle of the said orbital step is greater than the angle subtended by the said fan shaped spread by an integral multiple thereof and gaps in the information left thereby during the first 180° of orbital motion are filled, at least in part, in the course of the subsequent orbital motion.

In order that the invention may be clearly understood and readily carried into effect examples thereof will now be described with reference to the accompanying drawings of which:

Figure 1:
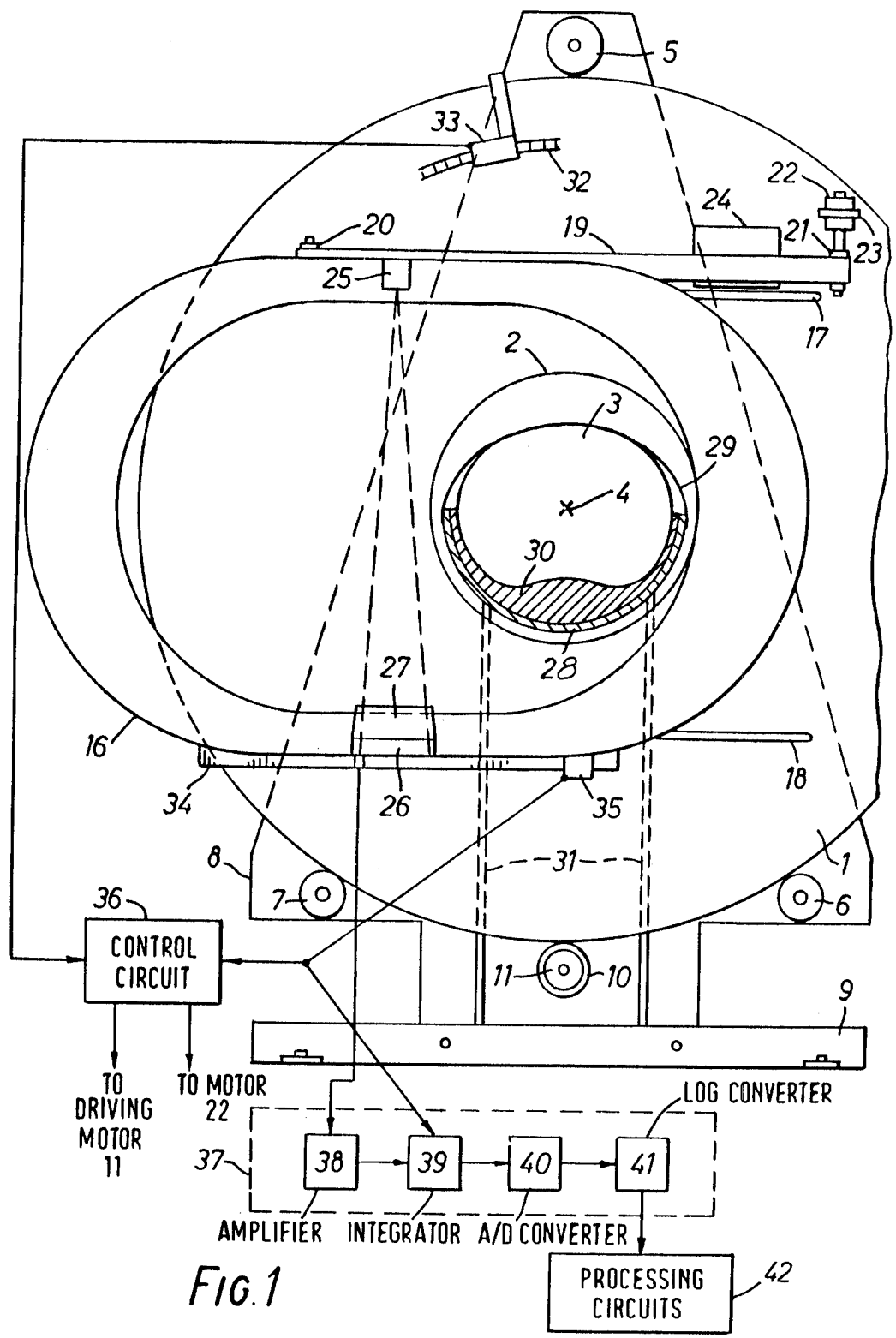
FIG. 1 shows an apparatus incorporating the invention.

Referring now to FIG. 1, the apparatus shown therein is similar in principle to the apparatus described in the aforementioned U.S. Pat. No. 3,946,234, except in the respect which will be described in greater detail hereinafter. A turntable member 1 having a central aperture 2, to accommodate a body 3 which is to be examined, is mounted vertically for rotation about an axis 4. Asix 4 is disposed centrally in the aperture 2. The member 1 is supported on three rotatable bearings 5, 6 and 7 which are journalled in the main frame 8 of the apparatus. The frame 8 remains stationary, being rigidly secured to a pedestal 9, and can take any suitable form, although it must of course be formed with an aperture coincident with the aperture 2.

The member 1 can be rotated in angular steps, as will be described hereinafter by means of a cog wheel 10 cooperating with gear teeth, not shown, cut into the periphery of the member 1. Cog wheel 10 is driven by a motor 11 which is fixed to main frame 8. If desired the gear teeth may take the form of slots so that the arrangement takes the form of a so called "Geneva mechanism" with cog wheel 10 being replaced by a rotating peg such as is used with that mechanism.

Mounted on the turntable 1, and capable of performing a reciprocating lateral scanning motion relative thereto, is a lightweight but rigid scanning yoke 16. Yoke 16 can run on linear runners 17 and 18 which are fixedly mounted on the rotable member 1 and are disposed chordally thereof. The lateral scanning motion is imparted to the yoke 16 by virtue of a toothed belt 19, which is stretched between a pair of toothed rollers 20 and 21 journalled in respective brackets, not shown, secured to the member 1. Yoke 16 is attached to belt 19 by means of a bracket, not shown. The roller 20 is merely an idler roller, but roller 21 is driven by a reciprocating motor 22 which is attached by a strap-like bracket 23 to the member 1.

A counter balance weight 24 is secured to the opposite run, of belt 19, to the yoke 16 and thus moves in opposition thereto to compensate for out-of-balance forces which would otherwise be set up by the lateral scanning motion of the york 16 and certain equipment mounted thereon, which will not be described.

Attached to the yoke 16 is a source 25 of penetrating radiation, in this example X-radiation. The radiation is collimated to form a planar, fan-shaped spread of radiation, emanating from an effective point source. On the opposite side of yoke 16, with respect to the aperture 2, to the source 25 is an array 26 of 36 detectors sensitive to the radiation generated by the source 25, each viewing the source through a respective collimator; the collimators being disposed in a bank 27. In this example, neighbouring collimators are inclined to each other at an angle of $\frac{1}{3}°$. Since there are 36 detectors this means that the angular spread of the beam of X-rays generated by the source is $11\frac{2}{3}°$ between the centre lines of the extreme beams. As will be made clear later, the beam is not symmetrical about the perpendicular line drawn from the effective point source of the beam of X-radiation to the array 26. This line is in fact arranged to intersect the nineteenth detector in the array 26, in this example, counting from the left in FIG. 1.

The body 3 is supported on a semicylindrical, one part bed 28 and is secured thereon by means of straps such as 29. Gaps between the body and the bed are filled with a suitable packing material 30 which is preferably of dough like consistency and absorbs the X-radiation to substantially the same extent as does human tissue. The material 30 is preferably contained in one or more plastic bags. The bed 28 is supported by legs 31 which stand on the pedestal 9.

As in the aforesaid U.S. Pat. No. 3,946,234, the rotational scanning motion, imparted by the cog wheel 10 to the member 1, needs to be synchronised with the lateral scanning motion imparted to the yoke 16 by the reciprocating motor 22. To this end the member 1 is formed with an annular graticule, part of which is shown at 32, and a fixed photodetector 33 which with a light source, not shown, is mounted on main frame 8. Photodetector 33 provides timing pulses indicative of the passage of markings on the graticule 32 past the photodetector 33. Thus the rotational scanning motion of member 1 is monitored. Similarly a linear graticule 34 is fixedly attached to the yoke 16 and cooperates with a second photodetector 35, which is mounted on the member 1 so as to rotate therewith, and a similarly mounted light source, not shown, to produce timing pulses indicative of the progress of the lateral scanning. Both graticules 32 and 34 comprise translucent or transparent members bearing opaque lines printed, etched or otherwise provided thereon. The two sets of timing pulses are fed to a control circuit 36 which controls the motor 22 and the motor 11 in such a way that, after each step of rotational motion, a single lateral scan is carried out to traverse the source 25 and the detector array 26 in one direction or the other across the aperture 2. Thus a single lateral scan is carried out for each dwell angle of the member 1.

Each detector in the array 26 comprises, for example a scintillator crystal, such as sodium iodide, and an associated photomultiplier tube, or a photodiode, and thus provides electrical signals indicative of the amount of radiation detected thereby. The electrical signals so provided are applied to respective pre-processing circuits 37, each of which contains an amplifier 38, a resettable integrator 39, an analogue-to-digital converter 40 and a logarithmic converter 41. The integrators 39 are read and reset synchronously and periodically by means of timing pulses derived from the photodetector 35; the arrangement in this example being such that the reading and re-setting occurs some one hundred and sixty times during each lateral scan in either direction. Thus, during a single lateral scan, output signals are provided which are indicative of the absorption suffered by the X-radiation on traversing a set of one hundred and sixty parallel paths from the source to the detector at each of 36 angular orientations with respect to the body 3. The member 1 is then rotated through, in this example of the invention, twenty four degrees and a second group of 36 sets of one hundred and sixty output signals are derived. The process is repeated until the member 1 has been rotated through at least 336° and all of the output signals obtained during the scanning are processed in a processing circuit 42 to evaluate the absorption coefficient, with respect to the radiation used, at a plurality of locations distributed over the slice of the body 3 which lies in the plane of the beam of X-rays generated by the source 25.

Preferably the processing is carried out in accordance with the technique described and claimed in U.S. Pat. No. 3,924,129 which involves a form of convolution. In practicing this technique the output signals derived from log converters 41 are assembled in sets relating to parallel paths through the body. Each output signal is then modified by combining it with weighted components of other output signals of its own set; the weighting being in accordance with a function which is negative, and decreases in amplitude as the distance from the path giving rise to the output signal being weighted to the path giving rise to the output signals being modified increases. The modified output signals are then additively combined in accordance with a layergramming procedure; the modification of the output signals being such as to compensate for the known inaccuracies of conventional layergrams. In relation to a predetermined point in the slice being examined the arrangement is such that the modified absorption values for all beam paths passing through, or near to, that point are combined to give an absorption coefficient for the point. In practice beams at the angular dispositions of all of the parallel sets of paths may not pass sufficiently close to each such evaluation point. For this reason interpolation is applied to the modified data for each parallel set of paths to obtain modified data for a new set of an increased number of such paths to ensure that at least one passes sufficiently close to each evaluation point.

Figure 2:
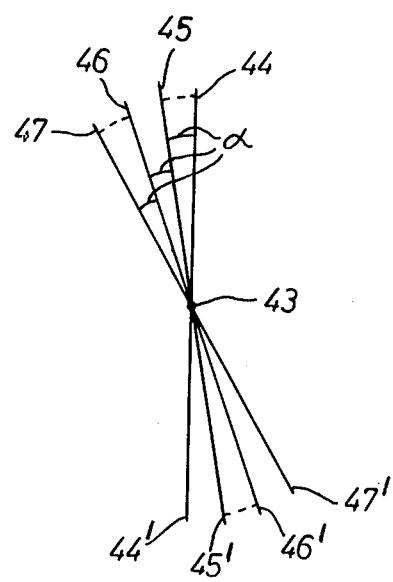
FIG. 2 is a diagram used to explain the invention.

As mentioned hereinbefore, the particular example described in detail in the said U.S. Pat. No. 3,946,234 was such that the orbital step was substantially equal to the total fan angle. Thus the angular distribution of beam paths was completed at substantially even spacing over a total angle of 180°. The situation is illustrated in FIG. 2 for beams through a typical evaluation point 43 in the slice. Assuming the total fan angle to be nearly $\alpha$ degrees from centre line to centre line, usually $9\frac{2}{3}°$ where $\alpha$ is 10°, one lateral scan will provide, through each point such as 43, data for beam paths between limits 44 and 45, as a result of the angular distribution of beams within the fan. It will be understood that the individual data will not be provided by the same detector or at one time and also that they may be interpolated values or may not pass exactly through point 43.

An orbital step of $\alpha°$ now takes place so that a further lateral scan provides data for beam paths between limits 45 and 46 and further steps give data for limits 46 and 47 and so on.

It will be seen that each beam passes through regions to two sides of point 43 so that m-1 angular steps, where $m\alpha = 180°$ is sufficient to provide equally angularly spaced beams passing through or close to point 43 over a complete spread of 360°.

The arrangement of the present invention provides an alternative to the scanning arrangement described in the immediately preceding three paragraphs. The angular step is arranged to be a multiple of the angle α so that successive angular steps leave sectoral gaps in which no beam paths are provided for the first 180° of rotation. The angular step is however arranged so that, if the rotation is extended through 360°, 720° or more as desired, the sectors for which beam path data are then provided will fall into the gaps previously left.

In a preferred embodiment of the invention the angle α is arranged to be twelve degrees and thirty six detectors provide beams at ⅓° angular spacing (centreline to centreline) over a total angular spread of 11⅔°. The motor 11 is then arranged to operate in conjunction with control circuit 36 so that member 1 and the equipment mounted thereon turn through approximately 24° between each lateral scan. Referring to FIG. 2 it will be apparent that the first lateral scan produces beam paths through point 43 distributed in angle between limits 44 and 45, joined by a dashed arc, as before. These limits are separated by α° (i.e. 12° in this example). Then after a rotary movement of 24° (i.e. 2 α) the next lateral scan provides beams distributed in angle between limits 46 and 47 also joined by a dashed arc. Thus there is a gap between limits 45 and 46 for which beams are not provided. This intermittent provision of beams extends for 180° whereupon it will be seen that a gap falls within the limits 44' and 45' but the next lateral scan provides beams in the gap between limits 45' and 46' as indicated again by a dashed arc and succeeding lateral scans fill in the other gaps. In the second 180° of rotation the radiation does of course travel in the opposite direction to that in which it would have travelled in the missing sectors. However this is not significant since it travels along substantially the same paths.

It will be seen that there are many related fan angles and orbital step angles for which missing data may be supplied in the course of an extended orbital motion in accordance with the principle described hereinbefore.

The invention may be extended to examples wherein the data is intended to be acquired over a different angle than 180°. For example if the data is to be acquired over 360°, so that identical beam paths may be examined by radiation travelling in opposite directions, then the technique of the invention may be applied and the data acquired over 720° or more.

For examples in which the data would have originally been acquired over 180°, values for the fan angle α are given by the formula $\alpha = 180/n$ where $n$ is an integer. However not all of the values given by the above formula are suitable and, in general, if orbital steps of $k\alpha$ are to be performed (k being an integer) then values of α for which $n/k$ is also an integer are not suitable. If all gaps in the information are to be filled, by obtaining a substantially even distribution of beam paths over 360°, the total orbital angle should then be $(k \times 180 - \alpha)°$. This principle may be extended to original acquisition over 360° or more, by substituting the desired angle for 180° in the above formulae.

It is preferred that the total acquisition does not take an excessive number of revolutions. Other angles and numbers of revolutions may, however, be used if desired.

If desired the orbital motion need not be continued to provide data for all of the beam paths omitted as a result of the larger orbital step, provided that sufficient data is obtained to give a satisfactory final evaluation of the absorption coefficients for the examined slice.

Additional refinements may be made to the apparatus shown in FIG. 1 without departing from the scope of the invention. For example blocks of X-ray absorbent material could be disposed between the source 25 and the body 3 and between the body 3 and the detector array 26 to tend to reduce variations in the degree of absorption suffered by the radiation on traversing paths of different lengths through the body 3. Moreover the blocks may be arranged to impart a specified attenuation to the radiation when it traverses paths wholly outside the body 3 and its supporting bed so as to permit the sensitivities of the various detectors to be monitored. In this regard it is advantageous to the use the technique, disclosed in the aforementioned U.S. Pat. No. 3,946,234, in which reference readings for the detectors in one half of the fan-shaped beam of radiation are obtained at one side of the aperture 2 whilst those for detectors in the other half of the beams are obtained at the other side of the aperture 2.

In some circumstances, it can be difficult to physically accommodate the large number of detectors used in side-by-side relationship in the array 26 and in such cases it is desirable to stagger the detectors in distance from the source. The stagger should, of course, be kept to a minimum.

What we claim is:

1. An apparatus for examining a slice of a body by means of penetrating radiation including a source of a substantially planar fan shaped spread of radiation arranged to irradiate the slice, a plurality of detectors co-operating with respective collimators to determine the intensity of the radiation transmitted along a plurality of beams within said fan shaped spread, means for scanning the source and detectors to scan the said fan shaped spread laterally in the said slice to provide determinations of the intensity of radiation transmitted along a plurality of sets of substantially parallel paths, each set provided by one of said detectors in the course of the lateral scan and means for orbiting said source and detectors between successive lateral scans about a common axis intersecting the said slice wherein the angle of the said orbital step is greater than the angle subtended by the said fan shaped spread by an integral multiple thereof and gaps in the information left thereby during the first 180° of orbital motion are filled, at least in part, in the course of the subsequent orbital motion.

2. Apparatus according to claim 1 wherein the angle, α°, subtended by the fan shaped spread is given by $\alpha = 180°/n$ where $n$ is an integer and the said orbital step is through $k\alpha°$ where $k$ is an integer, $n$ and $k$ being such that $n/k$ is not an integer.

3. Apparatus according to claim 2 wherein the total orbital motion is through an angle of $(k \times 180° - \alpha)°$.

4. Medical radiographic apparatus, for examining a slice of the body of a patient by means of penetrating radiation, including:

means defining a patient position for receiving said body; source means arranged to provide a fan shaped spread of radiation intersecting the patient position and subtending a total angle of substantially α°, given by $\alpha = 180°/n$ where $n$ is an integer, at the source; a plurality of detectors adapted to receive radiation transmitted through the patient position along respective relatively narrow beam paths angularly distributed across the fan shaped spread and to provide output signals representative of absorption suffered by the radiation in passage through the patient position; a scanning frame on which the source and detectors are mounted; means for traversing the scanning frame, and with it the source and detectors, laterally in relation to the said slice; means for angularly moving the scanning frame, and with it the source and detectors, about an axis intersecting the slice through an angle $k\alpha°$ after each of a plurality of lateral scans, where $k$ is an integer and $n$ and $k$ are chosen such that $n/k$ is not an integer, the total angular motion for a plurality of lateral scans being through an angle of $(k \times 180° - \alpha)°$; and means for processing the output signal, provided by the detectors during the plurality of lateral scans to provide a representation of the distribution of absorption of the radiation in said slice.

5. An apparatus for examining a substantially planar slice of a body by penetrating radiation comprising: a source of a substantially planar, fan-shaped spread of penetrating radiation propagating along the plane of the slice; a plurality of detectors of the radiation disposed to receive the radiation from the source after said radiation has tranversed the slice, each detector receiving the radiation propagating along a different one of a plurality of beam paths within said spread of radiation; means for orbiting the source and detectors about a common axis transverse to and intersecting the slice; means for scanning the source and detectors within the plane of the slice at each of a succession of equiangularly spaced orbital positions of the source and detectors to cause each detector to receive, in the course of each scanning, radiation from the source along a set of mutually parallel beam paths, the successive sets for each detector intersecting each other; said orbiting means orbiting and the source and detectors through an orbital angle greater than 180° and the angular spacing between each pair of adjacent orbital positions being greater than the spread angle of said spread of radiation; each orbital position being different from any previous orbital position and from any position diametrically opposite any previous orbital position; and means for deriving from each detector an electrical output signal indicative of the radiation received by the detector along each beam path of said sets of parallel beam paths along which the detector receives radiation in the course of said scanning of the source and detectors, and electrical circuit means for combining said output signals to produce a representation of the distribution within said slice of a radiation-response characteristic; whereby in the course of the first 180° of orbiting each elemental area of the slice is irradiated along lines spaced angularly from each other by the angle between two successive orbital positions and in the course of orbiting after the first 180° the same elemental area is irradiated along lines intermediate said first-mentioned lines.

* * * * *

UNITED STATES PATENT AND TRADEMARK OFFICE
CERTIFICATE OF CORRECTION

PATENT NO. : 4,091,285
DATED : May 23, 1978
INVENTOR(S) : ALLAN BEATTIE LOGAN, GEOFFREY MARSH, and IAN ALEXANDER FLEMING It is certified that error appears in the above-identified patent and that said Letters Patent are hereby corrected as shown below:

Column 2, line 14, delete "not" and insert -- now --.
          line 27, delete "Asix" and insert -- Axis --.
          line 61, delete "york" and insert -- yoke --.
          line 62, delete "not" and insert -- now --.

Column 4, line 59, delete "and" (third occurrence) and insert -- to --.

Column 6, line 11, delete "the" (first occurrence).

Column 7, line 20 (Claim 5), delete "transversed" and insert -- traversed --.

Column 8, line 4 (Claim 5), delete "and".

Signed and Sealed this

Sixth Day of March 1979

[SEAL]

Attest:

RUTH C. MASON
*Attesting Officer*

DONALD W. BANNER
*Commissioner of Patents and Trademarks*